United States Patent [19]
Reader

[11] 3,969,394
[45] July 13, 1976

[54] POLYURETHANES

[75] Inventor: Arthur M. Reader, Waynesboro, Va.

[73] Assignee: Celanese Corporation, New York, N.Y.

[22] Filed: Sept. 16, 1974

[21] Appl. No.: 506,082

[52] U.S. Cl.................. 260/471 C; 260/2.5 AM; 260/77.5 AP; 260/454; 260/455 A; 260/470; 260/475 P
[51] Int. Cl.² ........................................ C07C 125/06
[58] Field of Search ........ 260/455 A, 471 C, 476 R, 260/470, 475 P

[56] References Cited
UNITED STATES PATENTS 3,872,057  3/1975  Pazos .............................. 260/476 R Primary Examiner—Richard L. Raymond

[57] ABSTRACT

Novel polyisocyanates are provided, and thermoplastic polyurethane resins are produced therefrom which are suitable as substrates for film, fiber and foam products.

3 Claims, No Drawings

POLYURETHANES

BACKGROUND OF THE INVENTION

The production of bis(hydroxyalkyl) esters of benzenedicarboxylic acids such as bis(2-hydroxyethyl) terephthalate has become of significant commerical importance in recent years because these diesters can be polymerized to form linear super polyesters. These polyesters such as polyethylene terephthalate are widely used in textiles, tire cord and the like.

The present invention has developed from the investigation of new polymeric compositions derived from bis(2-hydroxyethyl) terephthalate which is now an inexpensive and readily available commercial product. It was deemed desirable to endeavor to introduce the excellent properties of bis(2-hydroxyethyl) terephthalate into polymeric compositions which would have unique properties and versatility in applications commonly served by polyamide and polyurethane thermoplastic resins.

It is thus an object of the present invention to provide novel polyisocyanate compounds based on bis(2-hydroxyethyl) terephthalate.

It is another object of this invention to provide thermoplastic polyurethane resins containing repeating ester and amide connecting linkages in the polymeric structure.

It is another object of this invention to provide a method for producing novel polyurethane cellular materials in a one step procedure.

Other objects and advantages of the present invention will become apparent from the following description and examples.

DESCRIPTION OF THE INVENTION

One or more objects of the present invention are accomplished by production of polyisocyanate compounds corresponding to the formula:

wherein R is a polyvalent organic radical containing between 2 and about 22 carbon atoms; X is an oxygen or sulfur atom; and $m$ is a positive integer having a value of from 1 to about 5.

One method of producing the invention polyisocyanates is by the reaction of bis(2-hydroxyethyl) terephthalate with a molar excess of an isocyanato-derivative having the general formula:

R(NCX)$_{m+l}$ wherein R is a polyvalent organic radical containing between 2 and about 22 carbon atoms; X is an oxygen or sulfur atom; and $m$ is a positive integer having a value of 1 to about 5, preferably a value of 1 or 2.

The reactant R(NCX)$_{m+l}$ can be an aliphatic, cycloaliphatic or aromatic compound or a derivative thereof not containing any groups which interfere with the reaction with bis(2-hydroxyethyl) terephthalate. Illustrative of suitable R(NCX)$_{m+l}$ compounds are 1,2-diisocyanatoethane;
1,4-diisocyanatobutane; bis(3-isocyanatopropyl)ether;
bis(3-isocyanatopropyl)sulfide;
1,5-diisocyanato-2,2,4-trimethylepentane; 1,10-diisocyanatodecane;
bis(3-isocyanatopropyl)ether of 1,4-butylene glycol;
bis(isocyanatohexyl)sulfide; 1,4-diisocyanatobenzene;
2,4-diisocyanatotoluene; 1,3-diisocyanato-o-xylene;
2,4-diisocyanato-1-chlorobenzene;
2,4-diisocyanato-1-nitrobenzene;
3,6-diisocyanato-1,4-dichlorobenzene;
2,5-diisocyanato-1,4-dimethoxybenzene;
2,4-diisocyanato-1-isobutylbenzene;
2,4-diisocyanato-1-isobutoxybenzene;
1,4-diisocyanatocyclohexane; 1,5-diisocyanatonaphthalene;
1,3-bis(4-isocyanatophenyl)propane;
2,4-diisocyanato-1-methylcyclohexane;
bis(4-isocyanatocyclohexyl)methane;
bis(2-methyl-4-isocyanatohexyl)methane;
1,5-diisocyanatotetrahydronaphthalene;
ethylene glycol bias(4-isocyanatophenyl)ether;
diethylene glycol bis(4-isocyanatophenyl)ether;
4,4'-diisocyanatobiphenyl;
3,3'-dimethoxy-4,4'-diisocyanatobiphenyl;
bis(4-isocyanatophenyl)methane; 2,2-bis(4-isocyanatophenyl)propane;
cyclohexyl-bis(4-isocyanatophenyl)methane;
2,2'-diisocyanatobenzophenone; 2,4-diisocyanatodibenzyl;
2,7-diisocyanatofluorene; bis(4-isocyanatophenyl)sulfide;
bis(4-isocyanatophenyl)sulfone;
bis(2-methyl-4-isocyanatophenyl)disulfide;
2,4,6-triisocyanatotoluene; triisocyanatomesitylene;
1,3,7-triisocyanatonaphthalene;
bis(2,5-diisocyanato-4-methylphenyl)methane; the corresponding isothocyanate derivatives; and the like.

There are a variety of known methods for producing the bis(2-hydroxyethyl) terephthalate reactant of the invention process. Probably best known and most widely used methods for producing these esters of benzenedicarboxylic acids are those in which the acid is suspended in an inert liquid medium and then reacted with an alkylene oxide in the presence of a catalyst. For example, see U.S. Pat. 3,037,049, May 29, 1962, to Alexander A. Vaitekunas, which discloses the use of such liquid reaction mediums as aromatic hydrocarbons, ketones and dioxane and which discloses the use of tertiary amine catalysts. Also such patents as Belgian Pat. Nos. 666,527, Belgian Pat. 660,257, British Pat. Nos. 999,242, 1,029,669, German Pat. No. 1,157,623, French Pat. Nos. 1,415,134, 1,430,842, 1,408,874 and Netherlands Pat. Nos. 6,413,334, 6,506,220 and 6,508,415 disclose esterification processes wherein various reaction media such as hydrocarbons, halohydrocarbons, water, alcohols, nitriles and dimethylformamide-water are disclosed and wherein such catalysts as phosphines, arsines, quaternary ammonium compounds, stibines, amino acids, alkali sulfites, alkali chlorides and alkali nitrates are used as catalysts. More recent advances in methods for producing bis(2-hydroxyethyl) terephthalate are described in U.S. Pat. Nos. 3,548,031; 3,644,484; and 3,597,471. In order to obtain one preferred class of polyisocyanate compounds of the present invention suitable for conversion into films and fibers, a molar ratio of between about 1.5 and 10 moles of R(NCX)$_2$ per mole of bis(2-hydroxyethyl) terephthalate are combined under reactive conditions.

The main objective of the reaction is to condense each molecule of bis(2-hydroxyethyl) terephthalate with 2 molecules of $R(NCX)_2$ derivative. For example, the condensation of one mole of bis(2-hydroxyethyl) terephthalate with 2 moles of 2,4-toluylene diisocyanate yields a novel isocyanato-terminated derivative (and isomers) of the formula:

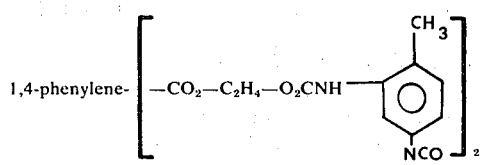

The control of the final product composition is best achieved by adding the bis(2-hydroxyethyl) terephthalate slowly to the $R(NCX)_{m+l}$ under reactive conditions. This procedure promoted the formation of the desired condensation product.

The reaction between bis(2-hydroxyethyl) terephthalate and $R(NCX)_{m+l}$ reactant can be accomplished over a wide range of temperatures. In most cases the reaction proceeds at or near room temperature, such as temperatures of up to about 150°C. Known catalysts for the isocyanate-hydroxyl condensation can be utilized to accelerate the reaction rate, e.g., triethylamine or tin salts, in an amount normally between about 0.05 and 2.0% by weight based on the weight of reactants.

The reaction between bis(2-hydroxyethyl) tereptha- late and $(R(NCX)_{m+l}$ can be performed conveniently at ambient pressure under a dry inert gas protective environment such as nitrogen or carbon dioxide. Inert diluents or solvents are employed as desired or necessary to enable proper handling and insure proper mixing of reactants. Recommended inert reaction media are tetrahydrofuran; dimethylformamide; dioxane; alkyl-substituted dioxolanes such as 2-propyldioxolane; the dialkyl ethers of alkylene glycols; benzene; toluene and xylene.

In another of this invention, an invention polyisocyanate compound as described hereinabove is reacted with an equivalent weight of polycarboxylic acid to produce a polyurethane resin having repeating ester and amide connecting linkages. Hence, in the polymeric chains there are contained structural moieties corresponding in kind to the basic structural unit in each of typical commercial polyester, polyamide and polyurethane resins. In terms of properties, the basic structural units of both Fortrel polyester and nylon polyamide are incorporated in the present invention polyurethane resins.

The polycarboxylic acids suitable for condensation with the invention polyisocyanate compounds include those corresponding to the formula:

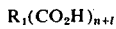

wherein $R_1$ is a polyvalent organic radical containing between 2 and about 12 carbon atoms; and $n$ is a positive integer having a value of 1 to about 5, preferably a value of 1 for polyurethane resins designed for film or fiber applications.

The reactant $R_1(CO_2H)_{n+1}$ can be an aliphatic, cycloaliphatic or aromatic compound. Illustrative of suitable $R_1(CO_2H)_{n+1}$ compounds are oxalic acid; succinic acid; glutaric acid; adipic acid; pimelic acid; sebacic acid; propylsuccinic acid; hexylsuccinic acid; maleic acid; chloromaleic acid; dichloromaleic acid; itaconic acid; citraconic acid; hexahydrophthalic acid; hexachlorophthalic acid; chlorendic acid; tetrabromophthalic acid; phthalic acid; terephthalic acid; 1,2-naphthalic dicarboxylic acid; 1,2,4,5-benzene-tetracarboxylic acid; polymeric derivatives of carboxylic acids such as maleic acid and itaconic acid; dimers of unsaturated fatty acids; trimers of drying oil acids; and the like.

It is a feature of the present invention that the polyurethane resins can be produced in one operation as essentially bubble-free films, fibers or coatings or produced as flexible or rigid cellular materials.

For the production of bubble-free plastics, the reaction medium is maintained in a low viscosity state. This may involve the addition of an organic solvent such as benzene, toluene, xylene, naphtha, carbon tetrachloride, ethyl acetate, amyl acetate, tetrahydrofuran, and the like. Conditions of low viscosity are essential in order that the carbon dioxide or carbon oxysulfide in the reaction medium is dissipated as it is generated by the condensation of polyisocyanate and polycarboxylic acid.

Cellular polyurethane materials are produced by maintaining the mixture of polyisocyanate and polycarboxylic acid in a relatively high viscosity state. The viscosity of the reaction medium should be sufficiently high to entrap the carbon dioxide or carbon oxysulfide as it is generated during the condensation reaction. In the cases where the foaming reaction is rapid, high speed mixing of components is advantageous.

If desired, the blowing action by the carbon dioxide or carbon oxysulfide can be supplemented by the use of a volatile halohydrocarbon, e.g., fluorochlorohydrocarbons such as trichlorofluoromethane and dichlorodifluoromethane. The heat evolved during the formation of the polyurethane resin is sufficient to vaporize the halohydrocarbon. The foaming can also be assisted by mechanical admixture of an inert gas.

Any suitable catalysts or emulsifiers can be included in the reaction mixture of polyisocyanate and polycarboxylic acid. Illustrative of catalysts are tertiary amines such as hexahydrodimethylaniline, triethylamine, N-ethylmorpholine, N-methyl-N'-dimethylaminoethylpiperazine, triethylene diamine, permethylated diethylene triamine, bis-aminoethanoladipate, tin salts of carboxylic acids such as stannous octoate, dibutyl tin dilaurate, stannous oleate, iron acetylacetonate and 1-azabicycloheptane and the like. It is preferred to use a foam stabilizer for the production of the cellular polyurethane plastics such as, for example, sulphonated castor oils and sodium salts thereof. Where polyhydric polyalkylene ethers are included in the reaction mixture to prepare a cellular polyurethane plastic, it is preferred to employ a silicone oil such as that disclosed in U.S. Pat. No. 2,834,748 within the scope of the formula:

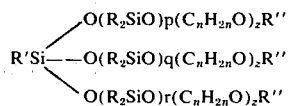

wherein R, R' and R'' are alkyl radicals having 1 to 4 carbon atoms; $p$, $q$ and $r$ each have a value of from 4 to 8 and $(C_nH_{2n}O)_z$ is a mixed polyoxyethylene oxypropylene group containing from 15 to 19 oxyethylene units and from 11 to 15 oxypropylene units with $z$ equal to from about 26 to about 34.

Light stabilizers, antioxidants, fillers, pigments, and the like, can be incorporated in the polyurethane materials as it is advantageous for individual applications.

The cellular polyurethane materials of the present invention find application as insulating and shock absorbing materials, depending on their special physical characteristics. The non-cellular polyurethane materials of the present invention are physically adaptable to be cast into sheets or films, drawn into fibers in the manner of polyesters and nylon polyamides, or coated on a substrate by dipping, brushing, roller coating, spraying, and the like. The low cost of starting materials, and the broad variety of important industrial applications which the herein described polyurethane resins can be adapted, are among the advantages derived by the practice of the present invention.

The following examples are further illustrative of the present invention. The reactants and other specific ingredients are presented as being typical, and various modification can be devised in view of the foregoing disclosure within the scope of the invention.

EXAMPLE 1

Preparation of Bis(2-hydroxyethyl) Terephthalate

A 3-liter autoclave is charged with 600 grams of crude terephthalic acid (3.61 moles), 1600 ml. of 2-propyldioxolane reaction medium, 0.11 mole of tetraethyl ammonium terephthalate catalyst and then purged with nitrogen. Liquid ethylene oxide (473 grams, 10.75 mole) is then pumped in and the reactor heated quickly to 155°C. by passing steam through internal coils. After about 3½ minutes the reaction is terminated by pressuring the contents of the autoclave into a vessel where the ethylene oxide is flashed and then the unreacted terephthalic acid removed by filtration. Cooling of the filtrate to about 18°C. yields about 742 grams of crude bis(2-hydroxyethyl) terephthalate.

EXAMPLE 2

Preparation of Catalyst For Bis(2-hydroxyethyl) Terephthalate Synthesis

A catalyst is prepared from Montrek 600E by mixing 24 grams of the material with 19.5 grams of terephthalic acid as well as 30 ml. of water so that good mixing can be obtained. After stirring the mixture for about 1 hour it is placed on a rotary film evaporator for the removal of the water and a thick solid recovered which is the terephthalic acid salt of the hydroxyethylated polyethyleneimine. Montrek 600E is Dow Chemical Company's designation for 40% aqueous solution of hydroxyethylated polyethyleneimine which is prepared by reacting polyethyleneimine having a molecular weight of about 40,000 to 60,000 with ethylene oxide.

EXAMPLE 3

Preparation of Bis(2-hydroxyethyl) Terephthalate

A 3-liter stirred autoclave is charged with 600 grams (3.6 moles) of fiber grade terephthalic acid, 1600 ml. chlorobenzene, 12.4 grams of the terephthalic acid salt of hydroxyethylated polyethyleneimine as prepared in Example 2, and then purged with nitrogen. Liquid ethylene oxide (8.6 moles is then pumped in and the reactor heated to 175°C. by passing steam through internal coils. The temperature is maintained at 175°C. for about 30 minutes with the pressure varying during thee period from about 215 p.s.i.g. at the beginning of the period to 80 p.s.i.g. at the end of the period. After the 30 minute period, the reaction is terminated by pressuring the contents of the autoclave into a vessel where ethylene oxide is flashed and then the unreacted terephthalic acid and other solids removed by filtration. Cooling of the filtrate to about 30°C. yields about 760 grams of bis(2-hydroxyethyl) terephthalate (dry basis). Conversion of the terephthalic acid charged to the diester product is about 91 mole percent.

EXAMPLE 4

Preparation of Polyisoxyanate

In a 500 ml. resin kettle equipped with stirrer, condenser with drying tube, thermometer, and nitrogen inlet, is placed 168 grams (1.0 mole) of hexamethylenediisocyanate dissolved in 300 ml. of 1,1,2,2-tetrachloroethane. To this is added 127 grams (0.5 moles) of bis(2-hydroxyethyl) terephthalate. The system is flushed with nitrogen, and the reaction is conducted with stirring under a nitrogen atmosphere. The temperature is slowly raised from room temperature to about 60° to 80°C. to insure complete reaction by bringing the reactants into solution. The mixture is maintained at temperature for 30 minutes.

The reaction product, which is a diisocyanate formed by "capping" 1 mole of bis(2-hydroxyethyl) terephthalate with two moles of hexamethylenediisocyanate is isolated by evaporating the 1,1,2,2-tetrachloroethane solvent under reduced pressure in a rotary evaporator. In some cases it is convenient to use the reaction product in solution without separating it from the solvent.

EXAMPLE 5

Preparation of Polyurethane Resin

The reaction product of Example 4, without isolating it from the S-tetrachloroethane solvent, is used as the starting material for a poly(ester/amide/urethane) of high molecular weight in the following manner.

The said reaction product is transferred to a 1000 ml. resin kettle, equipped similarly to the one of Example 4. One mole of adipic acid (146 grams) is added and the mixture is diluted with an additional 300 ml. of sym-tetrachloroethane to reduce the viscosity during reaction to permit evolution of carbon dioxide. The system is flushed with nitrogen and heated slowly with stirring under nitrogen using a heating mantle. The temperature is raised from room temperature at 2°–3° per minute to 80°C. and maintained at reaction temperature for one hour. Evaporation of the solvent produces a clear, tough polymer. Films cast from methylene chloride solution have excellent properties, and useful fibers are dry spun from this solvent.

EXAMPLE 6

Preparation of Polyisocyanate

In a 500 ml. resin kettle equipped with stirrer, condenser with drying tube, thermometer and nitrogen inlet, is placed 174 grams (1.0 mole) of 2,4-toluylene diisocyanate dissolved in 300 ml. of 1,1,2,2-tetrachloroethane. After flushing with nitrogen 127 grams (0.5 mole) of bis(2-hydroxyethyl) terephthalate is added. The reaction is conducted with stirring under nitrogen for ten minutes at room temperature. The temperature is then raised slowly to about 60° to 80°C. to insure complete reaction by bringing all reactants into solution. Reaction at elevated temperature is continued for 30 minutes.

The polyisocyanate reaction product is isolated by evaporating the solvent under reduced pressure in a rotary evaporator, or in some cases the polyisocyanate conveniently used in solution without further separation.

EXAMPLE 7

Preparation of Polyurethane Resins

The reaction mixturre of Example 6 is transferred to a 1000 ml. resin kettle equipped similarly to the resin kettle of Example 6 and diluted with 300 ml. of additional solvent. One mole of terephthalic acid (166 grams) is added. The system is flushed with nitrogen and heated with stirring at about 2°–3° per minute to about 80°C. The reaction is continued for one hour at that temperature under a nitrogen atmosphere. The polymer is isolated by evaporation of solvent under reduced pressure. The product, which is a very tough aromatic poly(ester-amide-urethane) is cast into tough clear films or spun into useful strong fibers from various common organic solvents.

Similar results are obtained if chlorendic acid is substituted for terephthalic acid in the above example.

EXAMPLE 8

One hundred parts of the polyisocyanate of Example 4 and an equivalent weight of maleic acid are dissolved in 50 parts of styrene, and the solution is stirred at 60°C. for 30 minutes. Additional styrene is added as needed to maintain adequate stirring action.

One percent ditertiarybutyl peroxide, based on the weight of reactants is added, and the solution is heated at 115°C. The resulting cured polyurethane product is hard and tough and has good resistance to solvents and water.

EXAMPLE 9

One hundred and fifty parts of the polyisocyanate of Example 4, 100 parts of adipic acid, 10 parts of ethylene glycol and 10 parts of tetrahydrofuran were mixed together. The resultant mixture is then mixed with 3 parts water, 0.2 parts of 1,4-diazobicyclo(2.2.2)octane and 1 part of a silicone oil (XL 520). The reaction mass is poured into a mold, and a semi-rigid polyurethane foam is obtained.

What is claimed is:
1. A polyisocyanate compound corresponding to the formula:

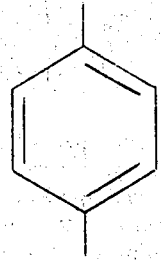
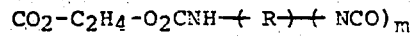

wherein R is a polyvalent organic radical containing between 2 and 22 carbon atoms selected from the group consisting of aliphatic, cycloaliphatic and aromatic radicals; and $m$ is a positive integer having a value of from 1 to about 5.

2. A polyisocyanate compound corresponding to the formula:

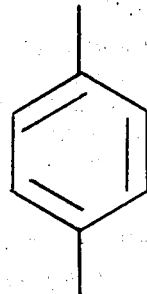
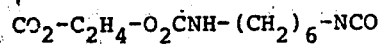

3. A polyisocyanate compound corresponding to the formula:

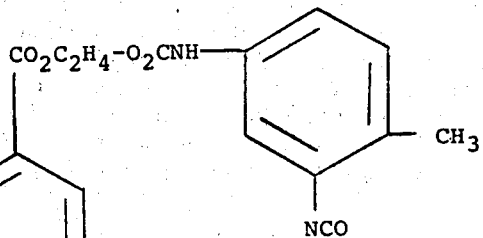
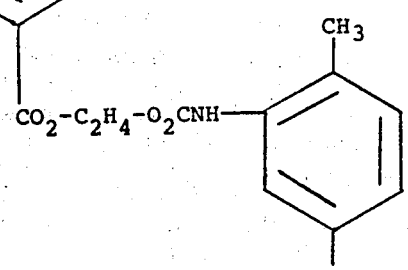

* * * * *